(12) United States Patent
Orth et al.

(10) Patent No.: US 7,779,693 B2
(45) Date of Patent: Aug. 24, 2010

(54) METHOD FOR NONDESTRUCTIVE TESTING OF PIPES FOR SURFACE FLAWS

(75) Inventors: Thomas Orth, Mülheim/a.d. Ruhr (DE); Stefan Nitsche, Mülheim/a.d. Ruhr (DE); Till Schmitte, Bochum (DE)

(73) Assignee: V & M Deutschland GmbH, Düsseldorf (DE)

( * ) Notice: Subject to any disclaimer, the term of this patent is extended or adjusted under 35 U.S.C. 154(b) by 343 days.

(21) Appl. No.: 11/997,043

(22) PCT Filed: Jul. 28, 2006

(86) PCT No.: PCT/DE2006/001362
§ 371 (c)(1),
(2), (4) Date: Jan. 28, 2008

(87) PCT Pub. No.: WO2007/012332
PCT Pub. Date: Feb. 1, 2007

(65) Prior Publication Data
US 2008/0210010 A1 Sep. 4, 2008

(30) Foreign Application Priority Data
Jul. 29, 2005 (DE) .................. 10 2005 036 509

(51) Int. Cl.
*G01N 29/00* (2006.01)
(52) U.S. Cl. ................ 73/622; 73/600; 73/602; 73/624; 73/627
(58) Field of Classification Search .......... 73/622, 73/620, 602, 624, 627
See application file for complete search history.

(56) References Cited

U.S. PATENT DOCUMENTS

| | | | | |
|---|---|---|---|---|
| 3,528,003 A | * | 9/1970 | Forster | 324/227 |
| 4,718,277 A | * | 1/1988 | Glascock | 73/622 |
| 4,901,578 A | * | 2/1990 | Brill, III | 73/623 |
| 5,100,610 A | * | 3/1992 | Pirl et al. | 376/260 |

(Continued)

FOREIGN PATENT DOCUMENTS

DE  100 65 093 A1  7/2002

(Continued)

OTHER PUBLICATIONS

Tucker R. W. et al.: "Characterization of gas pipeline flaws using wavelet analysis", Proceedings of the Spie, Sple, Bellingham, VA, US, vol. 5132, 2003, pp. 485-493, XP002375883.

(Continued)

*Primary Examiner*—J M Saint Surin
(74) *Attorney, Agent, or Firm*—Henry M. Feiereisen; Ursula B. Day

(57) ABSTRACT

A method for nondestructive testing of the pipes for detecting surface flaws is disclosed. With of the method, flaws can be detected and analyzed in near-real-time while the pipe is produced. The data obtained by ultrasound sensors are digitized in a time window following a trigger pulse, and the digitized data are processed in a digital processor, for example a DSP, using wavelet transforms. The evaluated quantity is compared with a reference value, wherein a determined flaw-based signal can be uniquely associated with the flaw located on the pipe surface.

6 Claims, 2 Drawing Sheets

U.S. PATENT DOCUMENTS

| | | | |
|---|---|---|---|
| 5,497,661 A * | 3/1996 | Stripf et al. | 73/611 |
| 6,622,561 B2 * | 9/2003 | Lam et al. | 73/622 |
| 6,643,406 B1 * | 11/2003 | Hajjahmad et al. | 382/240 |
| 6,748,808 B2 * | 6/2004 | Lam et al. | 73/622 |
| 6,772,636 B2 * | 8/2004 | Lam et al. | 73/622 |
| 7,111,516 B2 * | 9/2006 | Bazarov et al. | 73/623 |

FOREIGN PATENT DOCUMENTS

| | | |
|---|---|---|
| DE | 102 25 344 A1 | 12/2003 |
| JP | 09 210970 | 8/1997 |
| WO | WO 2005/012941 | 2/2005 |

OTHER PUBLICATIONS

Siqueira M.H.S. et al.: "The use of ultrasonic guided waves and wavelets analysis in pipe inspection", Ultrasonics, IPC Science and Technology Press Ltd., Guildford, GB, vol. 41, No. 10, May 10, 2004, pp. 785-797, XP004505102.

L-K Shark et al.: "Automatic estimation of ultrasonic attenuation for porosity evaluation in composite materials", Internet Citation, 2000, XP002301048, http://www.ndt.net/article/wcndt00/papers/idn223/idn223.htm>.

Aussel J-D et al.: "Structure noise reduction and deconvolution of ultrasonic data using wavelet decomposition (ultrasonic flaw detection)", 1989 Ultrasonics Symposium, Oct. 3, 1989, pp. 1139-1144, XP010090803, Canada.

* cited by examiner

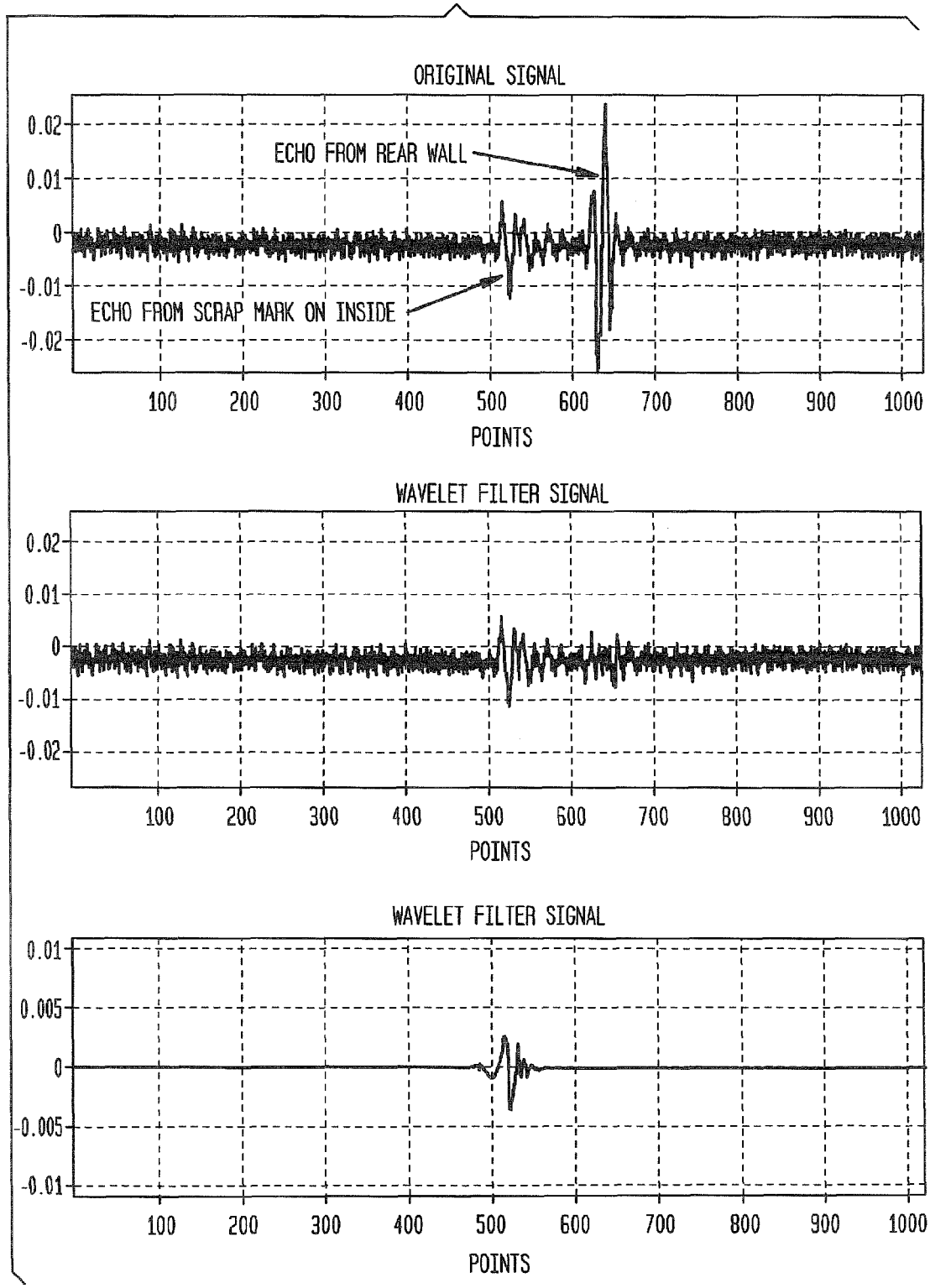

METHOD FOR NONDESTRUCTIVE TESTING OF PIPES FOR SURFACE FLAWS

BACKGROUND OF THE INVENTION

The invention is directed to a method for nondestructive testing of pipes for surface flaws.

Nondestructive methods for testing metal pipes for surface flaws, for example by ultrasound testing, are known for some time and have proven to be reliable.

Ultrasound tests are used in production to check, in particular, that the required wall thickness of the pipe is maintained and to detect potential discontinuities disposed in the pipe wall, for example laminations, cracks, grooves, scrap marks and other surface flaws.

With the pulse echo method, ultrasound pulses are excited in the wall during a test, starting from the exterior surface of the pipe, and the signals reflected by the interior surface of the pipe are received. The thickness of the pipe wall can be calculated from the transit time of the signal and the speed of sound in the tested material. This method is typically employed automatically during production for both magnetizable and non-magnetizable pipe materials.

This method has the disadvantage that, in particular, flaws on the interior side of the pipe, such as a bulges, which may very gradually taper on and off, could only be detected with great difficulty or not at all when employing the evaluation methods currently used in ultrasound testing.

For flaws having a curved surface, the ultrasound signals are reflected in different directions by scattering. The test head then receives the reflected ultrasound signals either not at all or not completely, so that a signal originating from a flaw is no longer unambiguously distinct from the inherent noise level of the signals and can therefore no longer be detected.

The method for detecting bulges disposed on the interior wall of the pipe, as disclosed in DE 100 65 093 A1, is also does not provide guidance. The method described therein is based on evaluating the reflected ultrasound signals to determine the magnitude by which the signal strength of the echo pulses (sequence of echoes from the rear wall) decreases. However, a bulge can still not be unambiguously identified by this method, because the decrease in the signal strength of the echo pulses may also have other causes, for example non-critical interior flaws or geometric effects.

It would therefore be desirable to investigate filter techniques suitable for separating flaw-based signals from the inherent noise level. In addition to digital filtering with conventional filtering algorithms, the so-called wavelet algorithms are particularly suited for this task. Instead of harmonic functions, wavelets are used as filter criteria because these can be very similar to the useful signals. By using wavelet filters, noise can be much more effectively reduced than with conventional filtering techniques.

It is generally known, for example from DE 102 25 344 A1, to use a wavelet transformation for evaluating time-dependent signals in industrial process monitoring to separate the noise components of the signals from the information components of the signals. In a wavelet transformation, which is an extension of the Fourier transformation, the original signal is projected onto wavelet basic functions, which corresponds to a transformation from the time domain to the time-frequency plane. The wavelet functions which are localized in the time domain and in the frequency domain, are derived from a single prototype wavelet, the so-called mother function, by dilatation and translation.

The intent is here to significantly reduce with the wavelet transformation the noise level compared to the signal caused by the flaw.

The conventional method discloses in general terms the advantages of applying of the wavelet algorithm to noise suppression for monitoring industrial processes. It is imperative with pipes produced in a continuous production process that the signals from the nondestructive testing are analyzed in near-real-time, so as to be able to immediately change the production process when flaws occur (for example, correlating the flaw by marking the pipe section or stopping the production process). However, DE 102 25 344 A1 does not address this issue.

WO 2005/012941 discloses a method for nondestructive testing of objects using ultrasound waves, wherein a wavelet transformation is used to reduce and/or compress the amount of data. Noise reduction or signal separation are not performed.

Therefore, there remains a problem during ultrasound testing in that surface test data of pipes must be measured and processed in near-real-time so as to allow intervention in the ongoing production process when flaws occur.

SUMMARY OF THE INVENTION

It is an object of the invention to provide a reliable and cost-effective method and a device for nondestructive testing of pipes with ultrasound, which can be used to measure and process the data related to surface flaws in the pipe in near-real-time by using a wavelet transformation.

The object is solved with the invention in that the signals are measured and processed the near-real-time by executing the following steps: Generating a continuous analog signal comprising the echoes from the rear wall, generating in addition to ultrasound signals a trigger signal, converting the analog signal into a digital signal pattern in a time window $t_1$ to $t_2$ having k data points, wherein the time $t_1$ can be set to occur subsequent to a trigger pulse, wherein the time $t_1$ is set so that the signal reflected from the other surface side with the expected flaw-based signal is located inside the time interval [$t_1$ to $t_2$], directly supplying the signal pattern to a digital computing unit for performing the wavelet transformation, optionally, digitally transmitting the filtered signal to a supervisory data processing system and evaluating the filtered signals at the supervisory data processing system, or evaluating the filtered signals at the digital computing unit, comparing the valuation variable with a reference value, wherein a determined flaw-based signal can be unambiguously associated with the flaw located at the pipe surface.

BRIEF DESCRIPTION OF THE DRAWING

The present invention will be more readily apparent upon reading the following description of currently preferred exemplified embodiments of the invention with reference to the accompanying drawing, in which:

FIG 2 is an exemplary diagram of a measurement signal of an ultrasound test for interior flaws of a pipe.

DETAILED DESCRIPTION OF PREFERRED EMBODIMENTS

Figure 1:
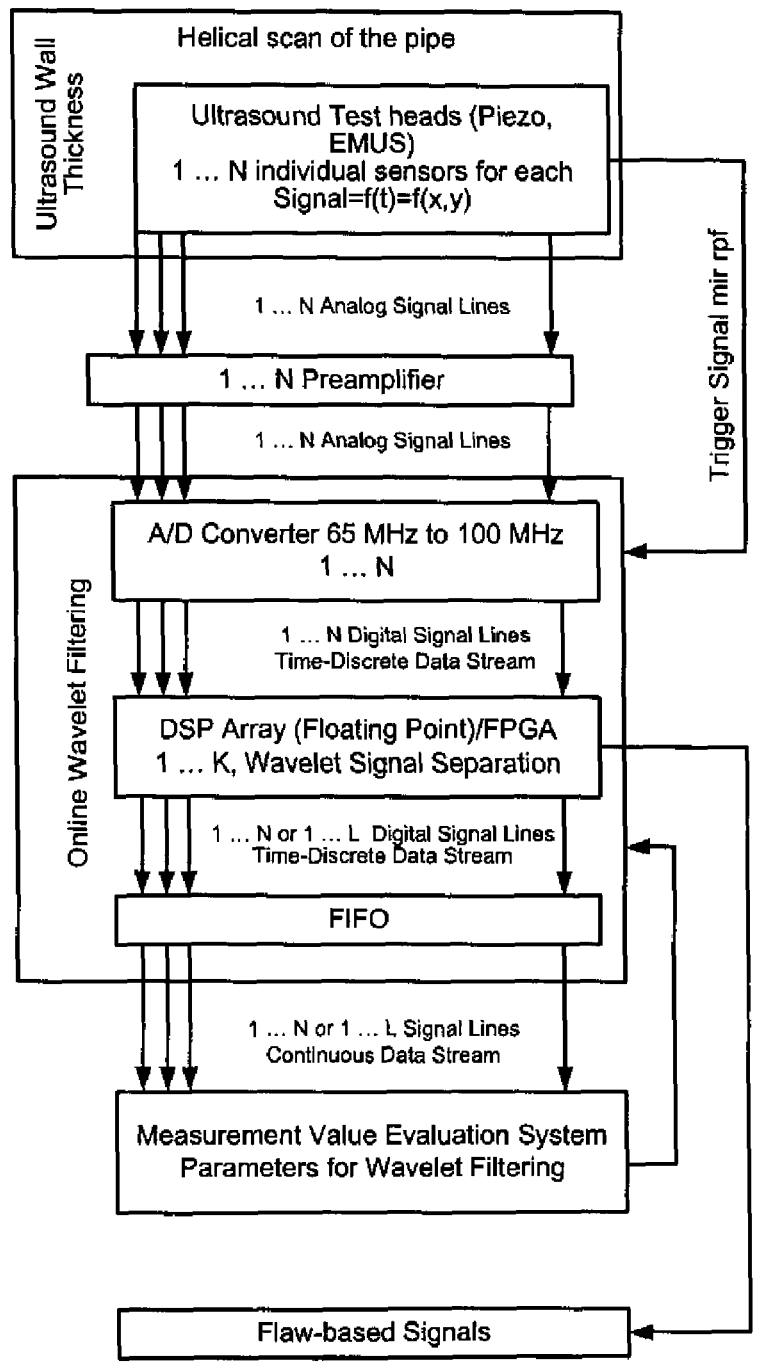
FIG. 1 is a flow chart illustrating a near-real-time measurement and processing of ultrasound signals by way of a signal pattern for an array having an arbitrary number of sensors.

Turning now to FIG. 1, there is shown a near-real-time measurement and processing of ultrasound signals by way of a signal pattern for an array having an arbitrary number of sensors.

The test head electronics of the ultrasound test head generates a continuous analog signal for each channel, wherein the signal includes, for example, the echoes from the rear wall. Due to the inherent characteristic of ultrasound technology, this signal includes components at very high frequencies. In addition to the ultrasound signals, a trigger signal is generated which represents the pulse repetition rate.

With an adjustable time t1 following a trigger pulse, a single curve with k data points is generated by using a fast A/D converter with the sampling rate f.

The signal pattern hereby represents the ultrasound signal in a time window from t1 to t2=k/f. The time t1 is here adjusted so that the echo from the rear wall with the expected flaw-based signal is located inside the interval [t1 t2].

The signal pattern is directly supplied for wavelet signal separation to a digital computing unit, which may advantageously be a digital signal processor (DSP).

The filter signals are transmitted digitally to a supervisory system, or the filtered signals are still further evaluated on the DSP, and if necessary, a flaw-based signal is generated.

In another advantageous embodiment of the afore-described method, the filtered signals are also converted by D/A filter and supplied to an existing system.

In another embodiment, several time windows of the afore-described type are placed over the input signal and digitized, so that several echoes can be evaluated. With this approach, the evaluated signal can be provided even more quickly.

FIG. 2 shows an exemplary diagram of a measurement signal of an ultrasound test for interior flaws of a pipe.

The upper section of the diagram shows a signal pattern from an electromagnetic ultrasound sensor (EMUS) with 1024 data points, wherein the amplitude of the signal is plotted as a function of time. Indicated on the signal pattern is the echo from the rear wall of the pipe and a flaw-based signal due to a scrap mark disposed on the inside of the pipe.

The smaller the distance between the flaw-based signal and the echo from the rear wall, i.e., the shallower the scrap mark, and the smaller the distinction the between the error amplitude and the noise level, the more difficult it becomes to separate the flaw-based signal from the echo originating at the rear wall.

For this reason, two wavelet transformation steps are carried out in parallel, whereby, as shown in the diagram in the center, the signal caused by the echo originating at the rear wall is filtered out, on one hand, and, as shown in the lower diagram, the inherent noise level is filtered out, on the other hand, thereby leaving only the actual flaw-based signal which can then be further processed.

What is claimed is:

1. A method for near-real-time nondestructive testing of metal pipes for flaws using ultrasound, comprising the steps of:
    moving a pipe longitudinally or rotationally, or both,
    scanning the pipe in a helical pattern with at least one first ultrasound test head disposed near a first surface of the pipe and generating ultrasound waves,
    measuring with the first ultrasound test head or with a second ultrasound test head a reflected ultrasound wave reflected by a second surface of the pipe or by a flaw disposed in the area proximate to the second surface,
    generating a continuous analog signal comprising an echo from a rear wall of the pipe,
    generating a trigger signal,
    converting the continuous analog signal into a digital signal profile in a time window t1 to t2 having k data points, wherein the time t1 is set to occur after the trigger signal, and the time window t1 to t2 includes the electric signal from the ultrasound wave reflected from the second surface of the pipe or the flaw,
    directly supplying the digital signal pattern to a digital computing unit for performing a wavelet transformation,
    digitally transmitting the wavelet-transformed signal to a supervisory data processing system and evaluating the filtered signals at the supervisory data processing system, or evaluating the filtered signals at the digital computing unit, and
    comparing a valuation variable derived from the evaluated filtered signals with a reference value for computing an flaw-based signal, and
    locating the flaw from the determined flaw-based signal.

2. The method of claim 1, wherein the flaw is selected from the group consisting of lamination, crack, groove, and scrap mark.

3. The method of claim 1, wherein the second surface is an interior surface of the pipe.

4. The method of claim 1, further comprising the step of marking a pipe section based on the flaw-based signal to indicate the flaw or stopping production of the pipe based on the flaw-based signal.

5. The method of claim 1, wherein the digital computing unit is a digital signal processor (DSP).

6. The method of claim 1, further comprising the steps of determining suitable wavelet basic functions that are matched to signals of the reflected ultrasound waves, and performing the wavelet transformation with the determined wavelet basic functions.

* * * * *